(12) United States Patent
Jallouli et al.

(10) Patent No.: US 7,732,507 B2
(45) Date of Patent: Jun. 8, 2010

(54) SPIROTETRATHIOCARBAMATES AND SPIROOXOTHIOCARBAMATES

(75) Inventors: Aref Jallouli, Largo, FL (US); Martin Rickwood, Clarks Green, PA (US); Kimberly Morgan, Moosic, PA (US); Sirisoma Wanigatunga, Largo, FL (US)

(73) Assignee: Essilor International Compagnie Generale d'Optique, Charenton-le-Pont (FR)

( * ) Notice: Subject to any disclaimer, the term of this patent is extended or adjusted under 35 U.S.C. 154(b) by 943 days.

(21) Appl. No.: 10/540,176

(22) PCT Filed: Dec. 19, 2003
(Under 37 CFR 1.47)

(86) PCT No.: PCT/EP03/15046
§ 371 (c)(1),
(2), (4) Date: Apr. 4, 2006

(87) PCT Pub. No.: WO2004/056879
PCT Pub. Date: Jul. 8, 2004

(65) Prior Publication Data
US 2008/0103230 A1 May 1, 2008

Related U.S. Application Data

(60) Provisional application No. 60/435,949, filed on Dec. 20, 2002.

(51) Int. Cl.
*G02B 1/04* (2006.01)
(52) U.S. Cl. .......................... 523/106; 549/29; 549/30; 549/31; 549/32; 549/35; 549/331; 549/333; 549/334
(58) Field of Classification Search ................. 523/106; 549/29–32, 35, 331, 333, 334
See application file for complete search history.

(56) References Cited

U.S. PATENT DOCUMENTS

| 3,525,752 A | 8/1970 | D'Amico et al. ............. 260/327 |
| 3,652,256 A | 3/1972 | D'Amico ....................... 70/90 |
| 3,787,370 A | 1/1974 | Shima et al. .................. 260/75 |
| 4,810,812 A | 3/1989 | Matsuda et al. ............. 558/251 |
| 5,021,541 A | 6/1991 | Masumoto et al. .......... 528/196 |
| 5,403,938 A | 4/1995 | Ohkubo et al. ............... 549/22 |
| 6,794,471 B2 | 9/2004 | Ohkuma et al. ............. 526/256 |

FOREIGN PATENT DOCUMENTS

| EP | 1193264 | 9/2001 |
| JP | 05105684 | 4/1993 |
| WO | WO 02/57339 | 1/2002 |
| WO | WO 02/051911 | 7/2002 |

OTHER PUBLICATIONS

Barbero et al., "Convenient procedure for converting 1,3-dithiolane-2-thiones into 1,3-dithiolan-2-ones," J. Chem Soc, Perkin Trans 1, pp. 289-294.
Coffen, "Transesterification of Orthothiocarbonates (1)," J. Heterocycl. Chem., 1970, 7, 201.
Moszner et al, "Polymerization of cyclic monomers, 1 Radical polymerization of unsaturated spiro orthocarbonates," Macromol. Rapid Commun. 16, 667-672 (1995).
Oremus et al., "145. 1,3-Oxathiolan-Synthese: Spirocyclische, 1,3-Oxathiolane aus der *Lewis*-Säure-katalysierten Umsetzung von cyclischen trithiocarbonaten and Oxiranen," Helvetica Chimica Acta, vol. 74 (1991).
Tagoshi and Endo, "Syntheses of Polyurethanes Containing a Spiroorthocarbonate Moiety in the Main Chain," Macromolecules 1989, 22, 3834-3838.
Takata and Endo, "A New Class of Polymerizable Sulfur Heterocycles. Cationic Ring-Opening Polymerization of Spiro Tetrathioorthocarbonate," Macromolecules 1988, 21, 2314.
Takata et al., "Cationic Ring-Opening Polymerizations of Five-Membered Spiro Orthocarbonates: Unsubstituted and 2,8-Diaryl-1,4,6,9-tetraoxaspiro[4.4]nonanes," Macromolecules 25 (1992).

*Primary Examiner*—Edward J Cain
(74) *Attorney, Agent, or Firm*—Fulbright & Jaworski L.L.P.

(57) ABSTRACT

Spirotetrathiocarbamates (STOCs) or oxa substituted compounds (SOTOCs) of Formula I: Formula (I) or bisSTOC or bisSOTOC compounds of Formula II: Formula (II) wherein $X^1, X^2, X^3, X^4, X^5, X^6, X^7$, and $X^8$, are independently O or S; and preferably at least two and up to all four of $X^1, X^2, X^3$ and $X^4$, and at least two and up to all four of $X^5, X^6, X^7$, and $X^8$ are sulfur; Z is $-C_mR^2{}_{2m}$ wherein m=1 to 4; $-C(R^2)_2SC(R^2)_2-$, $C(R^2)_2SSC(R^2)_2-$, or $-C(R^2)OC(R^2)_2$; n is from 0 to 4; M is selected from $CH_2Cl$, $CH_2SC(O)R^1$, $CH_2SC(S)R^1$, $CH_2S(CH_2CH_2S)qH$ wherein q is 0, 1 or 2; $-CR^2=CH_2$, $-CH_2OC(O)CR^2=CH_2$, $CH_2N=C=S$, $CH_2N=C=O$, $CH_2NR^2H$, $CH_2OH$, $CH_2SCH_2CH_2CR^2=CH_2$, phenyl, $C(R^2)$phenyl, furan, thiophene, halogen, $C_3$-$C_6$ cycloalkyl, $C_3$-$C_6$ heretocyclics, thiol, H, (III) or (IV) wherein A is S, O or phenyl; x is 0 or 1; $R^1$ is $C_1$-$C_{22}$ alkyl; and $R^2$ is H or $C_1$-$C_{22}$ alkyl have excellent optical properties. Methods for preparing these compositions and optical lenses prepared from the compounds are also provided.

26 Claims, No Drawings

SPIROTETRATHIOCARBAMATES AND SPIROOXOTHIOCARBAMATES

CROSS REFERENCE TO RELATED APPLICATIONS

This application is a national phase application under 35 U.S.C. §371 of International Application No. PCT/EP2003/015046 filed Dec. 19, 2003, which claims priority to U.S. Provisional Application No. 60/435,949 filed Dec. 20, 2002, the entire disclosures of which are incorporated herein by reference.

FIELD OF THE INVENTION

The present invention relates to monomers having suitable refractive characteristics useful in the preparation of optical resins or plastics suitable for, for example, the manufacture of hard ophthalmic lenses. More specifically, the invention relates to spirotetrathiocarbamate (STOCs) and their oxygen substituted derivatives spirooxothiocarbamates (SOTOCs), and their bis-derivatives (bisSTOCs or bisSOTOCs). The present invention is also directed to methods of making these compounds, optical devices containing the compounds, and methods for preparing these optical devices.

BACKGROUND OF THE INVENTION

In recent years, transparent synthetic resins having a high refractive index have found increasing applications as optical plastic materials replacing inorganic optical materials because of their light weight and good impact strength, moldability or processability and dyeability.

Plastics used in the preparation of optical devices must have properties suitable for the intended purpose. These materials should, inter alia, be transparent, non-yellowing, and have a suitable refractive index. In general, the higher the refractive index polymer allows for a thinner more lightweight lens, as well as an improved physical appearance. A refractive index of 1.5 or greater is desired, and higher refractive index plastics, e.g., 1.6, 1.7, 1.8, or more, are preferred.

Many different types of plastics are used to manufacture optical lenses, and these plastics are well-known in the art.

Further, some specific sulfur-containing, monomers have been described as useful for producing optical lenses with desirable refractive indices. For example, U.S. Pat. No. 4,810,812 discloses thiolcarboxylic acid esters which are said to have a high refractive index and suitable transparency. Additionally, 2,5-dimercaptomethyl 1,4-dithian of formula:

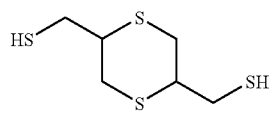

is disclosed in U.S. Pat. No. 5,403,938 and is said to be suitable for use in optical materials with high heat resistance and excellent mechanical properties as well as excellent optical properties.

An unsubstituted 4,4 spirotetrathiocarbamate compound having the formula:

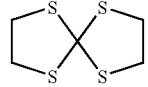

has been reported. The synthesis of the [4.4]STOC (above) is reported by D'Amico et al. in U.S. Pat. No. 3,525,752 and D'Amico in U.S. Pat. No. 3,652,256; and by D. L. Coffen, *J. Heterocycl. Chem.*, 7:201, 1970. Compounds of this type or partial or full oxa derivatives have been investigated with regard to expansion polymerization. T. Endo and T. Tanaka, *Macromolecules*, 21:2314, 1988.

A compound of formula:

has also been reported in M. Barbero, et al., *J. Chem Soc., Perkin Trans 1*, 3:289-94, 1996. The paper is concerned only with the biological activity of SOTOC precursors and derivatives.

There are also reports of polymerizing a 5,5 spirotetrathiocarbamate as shown below:

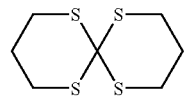

(See J. J. D'Amico et al. in U.S. Pat. No. 3,525,752 and D'Amico in U.S. Pat. No. 3,652,256; and D. L. Coffen, *J. Heterocycl. Chem.*, 7:201, 1970.)

U.S. Patent Application Publication 2002/0061995 discloses acrylic ester compounds of the general formula:

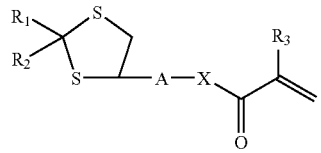

with specific substituents and polymerizable substituents bonded thereto. These compounds are said to be suitable resins for optical components having, inter alia, a high refractive index.

Despite the availability of a variety of optical polymers, new polymers with a high refractive index or other improved features are desirable.

SUMMARY OF THE INVENTION

It is an object of this invention, therefore, to provide monomers which can provide resins having a high refractive index and excellent transparency useful as an optical plastic material.

The present invention relates to substituted spirotetrathiocarbamate (STOCs) monomers and oxygen-substituted derivatives, known as spirooxothiocarbamates (SOTOCs), which have a suitable refractive index for use in preparing optical plastics. Compounds of the present invention have the general formula:

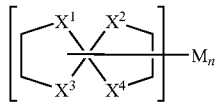

wherein $X^1$, $X^2$, $X^3$ and $X^4$ are O or S, wherein at least two and up to all four of $X^1$, $X^2$, $X^3$ and $X^4$ are sulfur (S);

n is from 1 to 4; and

M is selected from $CH_2Cl$, $CH_2SC(O)R^1$, $CH_2SC(S)R^1$, $CH_2S(CH_2CH_2S)qH$ wherein q is 0, 1 or 2; —$CR^2$=$CH_2$, —$CH_2OC(O)CR^2$=$CH_2$, $CH_2N$=C=S, $CH_2N$=C=O, $CH_2NR^2H$, $CH_2OH$, $CH_2SCH_2CH_2CR^2$=$CH_2$, phenyl, $C(R^2)_2$ phenyl, furan, thiophene, halogen, $C_3$-$C_6$ cycloalkyl, $C_3$-$C_6$ heterocyclics, thiol,

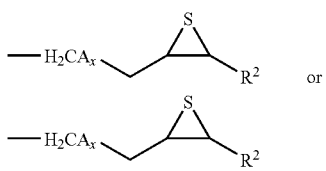

wherein A is S, O or phenyl and x is 0 or 1;

$R^1$ is $C_1$-$C_{22}$ alkyl; and $R^2$ is H or $C_1$-$C_{22}$ alkyl.

Additional spiro groups may attach to one or two positions of the STOC compound. Those Spiro moieties may be carbocyclic or heterocyclic (e.g., a sulfur heterocycle) in nature.

Alkyls of $C_1$-$C_{22}$, preferably $C_1$-$C_8$, most preferably $C_1$-$C_4$, are preferred substituents. Alkyls may be aliphatic or branched, substituted, e.g., with halogen, or unsubstituted. $C_1$ to $C_3$ aliphatic or $C_3$ to $C_6$ branched alkyls are preferred.

These materials may also undergo tandem double ring-opening polymerization under certain catalytic conditions, e.g. a cationic, and the resulting polymer species are also a part of the present invention. The ring-opening polymerization derivatives of species where M is $CH_2Cl$ or $CH_2SC(O)R^1$ are particularly preferred.

The invention also relates to bisSTOC and bisSOTOC compounds having the formula:

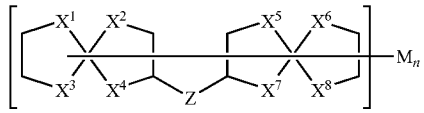

wherein $X^1$, $X^2$, $X^3$, $X^4$, $X^5$, $X^6$, $X^7$, and $X^8$, are independently O or S; and preferably at least two and up to all four of $X^1$, $X^2$, $X^3$ and $X^4$, and at least two and up to all four of $X^5$, $X^6$, $X^7$, and $X^8$ are sulfur(s).

n=0 to 4

Z is —$C_mR^2_{2m}$— wherein m=1-4; —$C(R^2)_2SC(R^2)_2$—, —$C(R^2)_2SSC(R^2)_2$—, or —$C(R^2)_2OC(R2)_2$;

M is selected from $CH_2Cl$, $CH_2SC(O)R^1$, $CH_2SC(S)R^1$, $CH_2S(CH_2CH_2S)qH$ wherein q is 0, 1 or 2; —$CR^2$=$CH_2$, —$CH_2OC(O)CR^2$=$CH_2$, $CH_2N$=C=S, $CH_2N$=C=O, $CH_2NR^2H$, $CH_2OH$, $CH_2SCH_2CH_2CR^2$=$CH_2$, phenyl, $C(R^2)_2$ phenyl, furan, thiophene, halogen, $C_3$-$C_6$ cycloalkyl, $C_3$-$C_6$ heterocyclics, thiol,

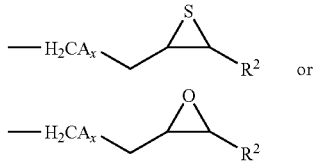

wherein A is S, O or phenyl and x is 0 or 1;

$R^1$ is $C_1$-$C_{22}$ alkyl; and $R^2$ is H or $C_1$-$C_{22}$ alkyl.

In a preferred embodiment, n=0, 1 or 2

By polymerizing the compounds of the invention, or copolymerizing them, various compounds can be made. The polymers have a high refractive index and excellent transparency, and have good processability characteristics such as machineability, and are suitable as optical plastics.

Methods for producing these compositions and optical lenses prepared from these compositions are also a part of the present invention. Optical lenses may be prepared by polymerizing or copolymerizing the compounds of the invention and forming an optical lens. Alternatively, optical lenses may be prepared by polymerizing or copolymerizing the compounds of the invention and coating an optical lens or suitable substrate therewith. The optical lenses are also a part of the invention.

DETAILED DESCRIPTION

In certain embodiments, the invention relates to STOC and SOTOC compounds of Formula I:

Formula I

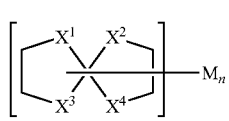

and bisSTOC and bisSOTOC compounds of Formula II:

Formula II

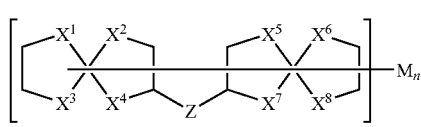

wherein $X^1$, $X^2$, $X^3$, $X^4$, $X^5$, $X^6$, $X^7$, and $X^8$, are independently O or S; and preferably at least two and up to all four of $X^1$, $X^2$, $X^3$ and $X^4$, and at least two and up to all four of $X^5$, $X^6$, $X^7$, and $X^8$ are sulfur(s);

Z is —$C_mR^2_{2m}$— wherein m=1-4; —$C(R^2)_2SC(R^2)_2$—, —$C(R^2)_2SSC(R^2)_2$—, or —$C(R^2)_2OC(R^2)_2$;

n is from 0 to 4; and

M is selected from $CH_2Cl$, $CH_2SC(O)R^1$, $CH_2SC(S)R^1$, $CH_2S(CH_2CH_2S)qH$ wherein q is 0, 1 or 2; —$CR^2$=$CH_2$, —$CH_2OC(O)CR^2$=$CH_2$, $CH_2N$=C=S, $CH_2N$=C=O, $CH_2NR^2H$, $CH_2OH$, $CH_2SCH_2CH_2CR^2=CH_2$, phenyl, $C(R^2)_2$ phenyl, furan, thiophene, halogen, $C_3$-$C_6$ cycloalkyl, $C_3$-$C_6$ heretocyclics, thiol, H,

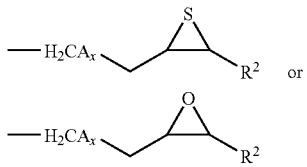

wherein A is S, O or phenyl and x is 0 or 1;
$R^1$ is $C_1$-$C_{22}$ alkyl; and
$R^2$ is H or $C_1$-$C_{22}$ alkyl, Except that if the compound is a STOC or SOTOC, at least one M substituent cannot be H and n must be 1, 2, 3 or 4.

Preferably, M is H, $CH_2SH$, $CH_2Cl$, $CH_2SCOCH_3$ or $CH=CH_2$. Also preferably, n is 1 or 2.

In general, the compounds of formula I can be prepared according to the following reaction scheme:

(Reaction 1)

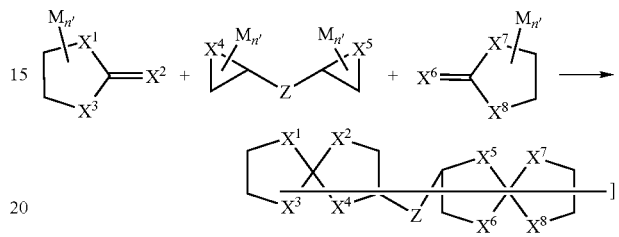

$X^1$, $X^2$, $X^3$, $X^4$, M and n being defined as above, and n1 and n2 being 0, 1 or 2 with the provision that n1+n2.0 and at least one M substituent is not H.

In a preferred embodiment, the compounds of Formula I may be prepared as follows:

(Reaction 2)

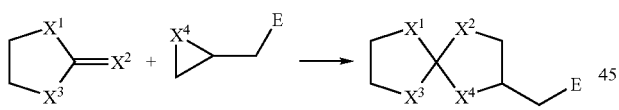

wherein $X^1$, $X^2$, $X^3$ and $X^4$ are as defined above, and E is halide or thiol.

Another preferred method for producing the compounds according to Formula I is set forth below:

(Reaction 3)

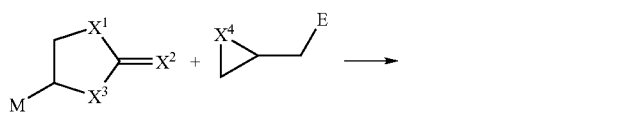

wherein $X^1$, $X^2$, $X^3$ and $X^4$ and E are as defined above, and M is as defined above.

The reaction temperatures may range from −10 to 70. C, with the reaction temperature being determined by the stability of the reactions and products and other factors known to those skilled in the art.

Solvents and catalysts will be selected according to the reactants and other factors known to those skilled in the art.

The bisTOCs and bisSOTOCs of the present invention may be prepared according to the following reaction schemes:

(Reaction 4)

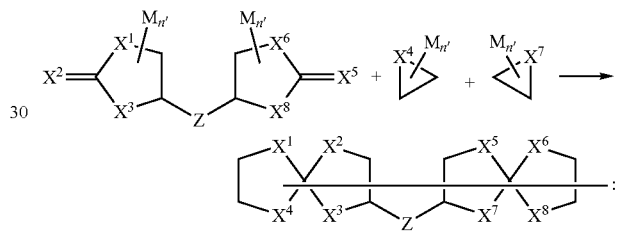

(Reaction 5)

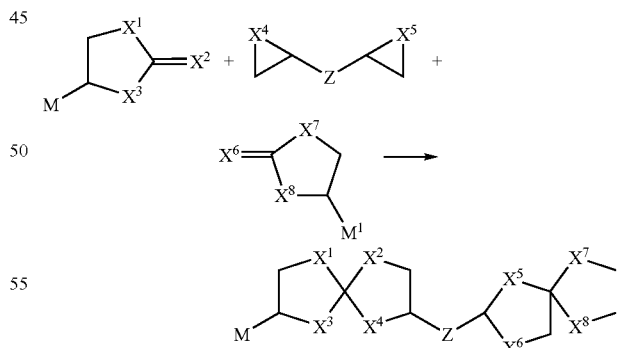

With n' being 0, 1 or 2, $X^1$, $X^2$, $X^3$, $X^4$, $X^5$, $X^6$, $X^7$ and $X^8$, Z, M and n having the definition provided above.

The bisSTOCs and bisSOTOCs of the present invention may preferably be prepared, e.g., by the reaction set forth below:

(Reaction 6)

wherein $X^1$, $X^2$, $X^3$, $X^4$, $X^5$, $X^6$, $X^7$, $X^8$, Z and M have the definitions provided above. $M^1$ may be $CH_2Cl$, $CH_2SC(O)R^1$, $CH_2SC(S)R^1$, $CH_2S(CH_2CH_2S)qH$ wherein q is 0, 1 or 2, $-CR^2=CH_2$, $-CH_2OC(O)CR^2=CH_2$, $CH_2N=C=S$, $CH_2N=C=O$, $CH_2NR^2H$, $CH_2OH$, $CH_2SCH_2CH_2CR^2=CH_2$, phenyl, $C(R^2)$phenyl, furan, thiophene, halogen, $C_3$-$C_6$ cycloalkyl, $C_3$-$C_6$ heretocyclics, thiol, H

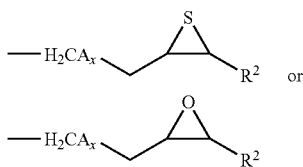

wherein A is S, O or phenyl and x is 0 or 1;
R[1] is $C_1$-$C_{22}$ alkyl; and
R[2] is H or $C_1$-$C_{22}$ alkyl.

Each of the alternative atoms or groups on the compounds of the invention are their precurser molecules independently selected so that the resulting bis compound may or may not be symmetrical. Thus, for example, M and M[1] may be the same or different.

It is preferred that the reaction be carried out in a suitable catalyst, e.g., tetrafluoroboric acid.

In a preferred embodiment, at least one substituted or unsubstituted ethylenetrithiocarbonate is reacted with bis-methylthiirane sulphide or bis-methylthiirane disulphide, in the presence of a catalytic amount of tetrafluoroboric acid to produce the desired bisSTOC.

An alternative embodiment for preparing bisSTOCs and bisSOTOCs is set forth below:

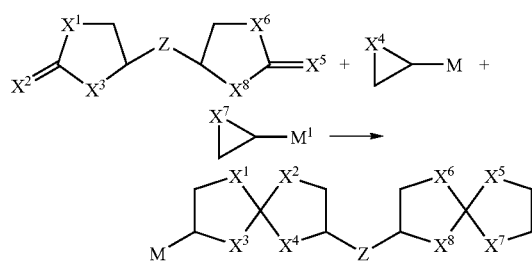

wherein $X^1, X^2, X^3, X^4, X^5, X^6, X^7, X^8, Z, M$ and $M^1$ are as defined above.

In a preferred embodiment, bis-ethylenetrithiocarbonate sulfide, or bis-ethylenetrithiocarbonate, is reacted with a substituted thiirane, in the presence of a catalytic amount of tetrafluoroboric acid to produce the desired bisSTOC.

In another preferred embodiment, bisSOTOCs of the present invention can be prepared by reacting a substituted or unsubstituted ethylenedithiocarbonate with bis-methylthiirane sulphide, or bis-methylthiirane disulphide, in the presence of a catalytic amount of tetrafluoroboric acid to produce the bisSOTOC. A schematic of the reaction is provided below:

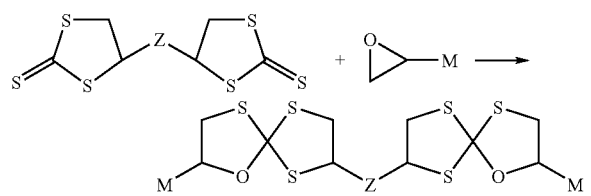

wherein Z is preferably —$CH_2SCH_2$— or —$CH_2SSCH_2$—.

Alternatively, bisSOTOCs of the present invention may be prepared by reacting bis-ethylenetrithiocarbonate sulfide or bis-ethylenetrithiocarbonate, with substituted oxirane, in the presence of a catalytic amount of tetrafluoroboric acid to produce the bisSOTOC.

The compositions of the present invention may have one or more chiral centers.

The compositions of the present invention may have enantiomers and diastereoisomers that are contemplated to be within the scope of the present invention. Examples of enantiomers and diastereoisomers are shown in Tables 1 and 2 below:

TABLE 1

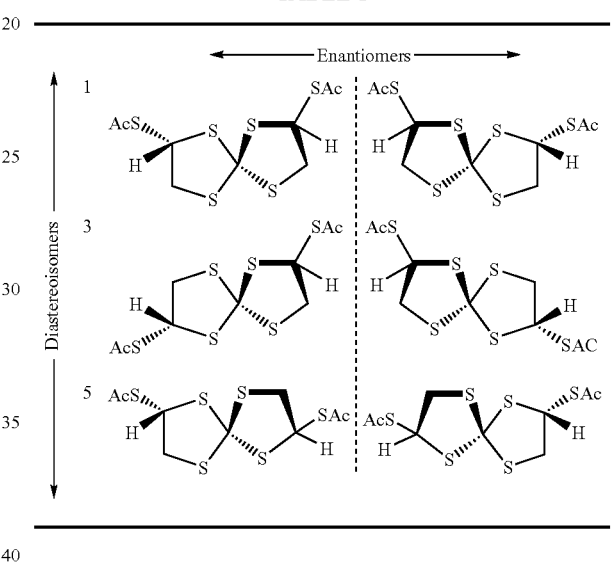

TABLE 2

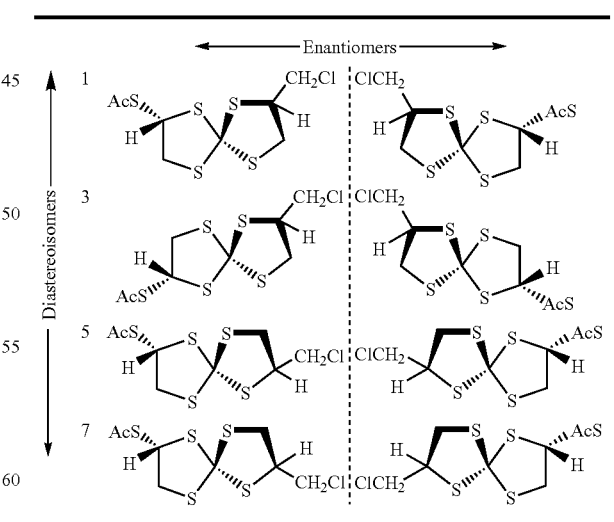

Given the novel STOC and SOTOC compounds disclosed herein, those of ordinary skill will be able to prepare a variety of polymeric substrates useful for optics using a variety of known methods.

Preferred embodiments of the invention are discussed in detail below.

Preparation of STOC and SOTOC Compounds

Example 1

Preparation of 2-Mercaptomethyl)-1,4,6,9-tetrathiaspiro[4.4]nonane (1a)

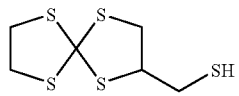

(1a)

A. Preparation of 2-(Chloromethyl)-1,4,6,9-tetrathiaspiro[4.4]nonane (1b)

A stirred, cooled (−5° C. ice-salt), solution of ethylene trithiocarbonate (12.03 g; 0.088 moles) and tetrafluoroboric acid (2.2 mL) in anhydrous dichloromethane (160 mL) under nitrogen, was treated drop-wise with a solution of epithiochlorohydrin (11.52 g; 0.106 moles) in anhydrous dichloromethane (160 mL). The reaction was allowed to warm to room temperature and left to stir for 22 hours.

The reaction mixture was washed with 5% aqueous sodium bicarbonate solution and the organic layer separated, dried and evaporated to yield a wet yellow solid. Trituration with hexane afforded 2-(chloromethyl)-1,4,6,9-tetrathiaspiro[4.4]nonane as a yellow solid (yield 82.0%).

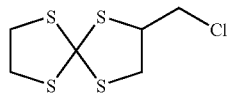

(1b)

M.p.=71-77° C.
H-NMR analysis provided the following data:
$^1$H-NMR (CDCl$_3$): 3.36-3.49 (m, 4H, H-7 and H-8), 3.57-3.65 (m, 3H, H-3, CH$_2$Cl), 3.95 (dd, 1H, H-3), 4.06 (m, 1H, H-2).
$^{13}$C-NMR (CDCl$_3$): 42.43 and 42.68 (C(7 and 8)), 44.38 (CH$_2$Cl), 44.93 (C(3)), 58.40 (C(2)), 85.88 (C(5)).

B. Preparation of 2-(S-Methyl)-1,4,6,9-tetrathiaspiro[4.4]nonane thiolacetate (1c)

A solution of 2-(chloromethyl)-1,4,6,9-tetrathiaspiro[4.4] nonane (10.02 g; 0.041 moles) in anhydrous DMF (50.0 mL) was added drop-wise to a stirred solution of potassium thiolacetate (7.31 g; 0.064 moles) in dry DMF (240 mL) at room temperature under nitrogen. The resulting mixture was allowed to stir for 44 hours. The reaction mixture was evaporated, and the resulting wet solid taken up in chloroform and washed with water.

The organic layer was separated, dried and evaporated to yield a yellow solid. Purification by flash-chromatography (10% ethyl acetate in hexane over silica) afforded 2-(S-methyl)-1,4,6,9-tetrathiaspiro[4.4]nonane thiolacetate as a clear oil (yield 23.2%).

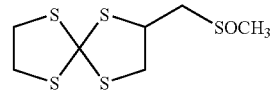

(1c)

$^1$H-NMR (CDCl$_3$): 2.36 (s, 3H, CH$_3$), 3.27-3.49 (m, 8H, H-3, H-7, H-8 and CH$_2$), 4.00 (m, 1H, H-2).
$^{13}$C-NMR (CDCl$_3$): 30.97 (CH$_3$), 33.18 (CH$_2$), 42.43 and 42.50 (C(7 and 8)), 46.03 (C(3)), 57.87 (C(2)), 83.50 (C(5)), 193.05 (CO).

C. Preparation of 2-(Mercaptomethyl)-1,4,6,9-tetrathiaspiro[4.4]nonane (1a)

A solution of 2-(S-methyl)-1,4,6,9-tetrathiaspiro[4.4] nonane thiolacetate (2.70 g; 0.009 moles) in anhydrous THF (50.0 mL) was added drop-wise to a cooled (ice-water) stirred solution of 1.0M Lithium Aluminum Hydride (5.92 mL; 0.006 moles) in THF under nitrogen. The subsequent mixture was allowed to warm to room temperature and stirred for a further 5 hours.

The reaction mixture was acidified and extracted with diethyl ether. The diethyl ether extract was washed first with water (1×75 mL), then with a saturated salt solution (1×75 mL). The organic phase was separated, dried and evaporated to give a yellow liquid which upon cooling and trituration with diethyl ether afforded crude 2-(mercaptomethyl)-1,4,6, 9-tetrathiaspiro[4.4]nonane as yellow solid (yield 37.6%). Recrystalization from hexane gave the product as a white solid.

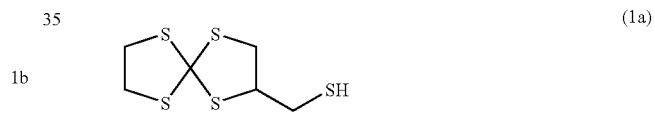

(1a)

M.p.=79 to 80.5° C.
$^1$H-NMR (CDCl$_3$): 1.67 (s, 1H, SH), 2.91-2.97 (m, 2H, CH$_2$), 3.38-3.50 (m, 5H, H-3, H-7 and H-8), 3.61 (dd, 1H, H-3), 3.97 (m, 1H, H-2).
$^{13}$C-NMR (CDCl$_3$): 27.13 (CH$_2$), 40.94 and 40.98 (C(7 and 8)), 43.87 (C(3)), 59.84 (C(2)), 84.15 (C(5)).

Example 2

Preparation of 2,7-Bis(mercaptomethyl)-1,4,6,9-tetrathiaspiro[4.4]nonane (2a)

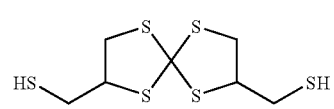

(2a)

Method 1

A. Preparation of 4-(S-Methyl)-1,3-dithiolane-2-thione thiolacetate (2b)

A stirred, cooled (ice-water), solution of triethylamine (32.57 g; 0.32 moles, 44.8 mL) and 2-(mercaptomethyl)-1,3- dithiolane-2-thione (40.48 g; 0.22 moles) in anhydrous THF (500 ml), under nitrogen, was treated drop-wise with a solution of acetyl chloride (20.91 g; 0.27 moles; 18.9 mL) in anhydrous THF (250 mL). The reaction mixture was allowed to warm to room temperature. The solid was collected and washed with diethyl ether. The ether filtrate was washed with water, separated, dried and evaporated to yield a wet brown solid (49.69 g). Trituration with diethyl ether afforded 2-(S-methyl)-1,3-dithiolane-2-thione thiolacetate as a yellow-brown solid (38.18 g; 76.7%).

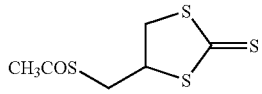

(2b)

M.p.=45° C. to 48° C.

$^1$H-NMR (CDCl$_3$): 2.41 (s, 3H, CH$_3$), 3.37-3.42 (m, 2H, CH$_2$), 3.80 (dd, 1H, H-5), 4.10 (dd, 1H, H-5), 4.45 (m, 1H, H-4).

$^{13}$C-NMR (CDCl$_3$): 30.32 (CH$_3$), 31.43 (CH$_2$), 46.64 (C(5)), 57.72 (C(4)), 194.07 (CO).

MS: 225 [M+H]$^+$

B. Production of 2-(Chloromethyl)-7-(S-methyl)-1,4,6,9-tetrathiaspiro[4.4]nonane Thiolacetate (2c)

A stirred, cooled (−5° C. ice-salt), solution of tetrafluoroboric acid (0.20 mL) and 4-(S-methyl)-1,3-dithiolane-2-thione thiolacetate (1.70 g; 0.008 moles) in anhydrous dichloromethane (50.0 mL), under nitrogen, was treated drop-wise with a solution of epithiochlorohydrin (1.70 g; 0.016 moles) in anhydrous dichloromethane (40.0 mL). The resulting mixture was allowed to warm to room temperature and left to stir for 22 hours.

The reaction mixture was treated with water (50.0 mL) and the organic phase separated, dried and evaporated to leave a brown-red oil. Purification by short-path chromatography (10% ethyl acetate in hexane over flash silica) yielded a diastereoisomeric mixture of 2-(chloromethyl)-7-(S-methyl)-1,4,6,9-tetrathiaspiro[4.4]nonane thiolacetate as pale yellow oil (yield 56.2%).

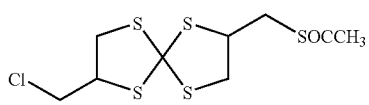

(2c)

$^1$H-NMR (CDCl$_3$): 2.37 (s, 3H, CH$_3$), 3.15-3.70 (m, 7H, H-3, H-8, CH$_2$S, CH$_2$Cl), 3.85-4.08 and 4.10-4.20 (m, 3H, H-2, H-7 and H-8)

$^{13}$C-NMR (CDCl$_3$): 31.03 (CH$_3$), 32.10-34.12 (CH$_2$S), 44.03-46.19 (C(3), (8) and CH$_2$Cl), 57.29-58.87 (C(2) and (7)), 85.39-85.82 (C(5)), 194.78-195.12 (CO).

MS: 225 and 333 [M+H]$^+$

C. Production of 2,7-Bis(S-methyl)-1,4,6,9-tetrathiaspiro[4.4]nonane Thiolacetate (2d)

A solution of 2-(chloromethyl)-7-(S-methyl)-1,4,6,9-tetrathiaspiro[4.4]nonane thiolacetate (0.91 g; 0.0027 moles) in anhydrous DMF (25.0 mL) was added drop-wise to a potassium thiolacetate (2.44 g; 0.021 moles) in dry DMF (45.0 mL). The reaction was stirred under nitrogen, at room temperature for 52 hours.

The resulting reaction mixture was evaporated, dissolved in chloroform and washed with water. The organic phase was separated, dried and evaporated to yield a diastereoisomeric mixture of 2,7-bis(S-methyl)-1,4,6,9-tetrathiaspiro[4.4] nonane thiolacetate as a yellow oil (yield 29.5%).

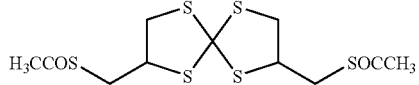

(2d)

$^1$H-NMR (CDCl$_3$): 2.36 (s, 6H, 2×CH$_3$), 3.25-3.40 (m, 6H, H-3, H-8, 2×CH$_2$), 3.45-3.55 (m, 2H, H-3, and H-8), 3.96 and 4.10 (m, 2H, H-2 and H-7).

$^{13}$C-NMR (CDCl$_3$): 30.96 (CH$_3$), 32.59-33.73 (CH$_2$S), 45.82-46.12 (C(3) and (8)), 57.49-58.33 (C(2) and (7)), 85.00-85.30 (C(5)), 195.04-195.12 (CO).

MS: 225 and 373 [M+H]$^+$

D. Production of 2,7-Bis(mercaptomethyl)-1,4,6,9-tetrathiaspiro[4.4]nonane (2a)

To a cooled (ice-water), stirred, solution of 1.0M LiAlH$_4$ (4.9 mL; 0.005 moles) in THF was added drop-wise to a solution of 2,7-bis(S methyl)-1,4,6,9-tetrathiaspiro[4.4] nonane thiolacetate (0.99 g; 0.0008 moles) in anhydrous THF (20.0 mL). The reaction mix was allowed to warm to room temperature and stir for a further 18 hours.

The reaction mixture was acidified to pH 4 with 10% sulfuric acid and extracted into diethyl ether. The diethyl ether fraction was separated, dried and evaporated to yield a brown oil. Purification by flash-chromatography (10% ethyl acetate in hexane over silica) afforded a diastereoisomeric mixture of 2,7-bis(mercaptomethyl)-1,4,6,9-tetrathiaspiro[4.4]nonane as a light yellow oil (yield 40.7%).

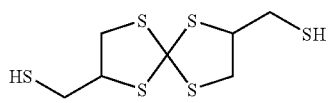

(2a)

$^1$H-NMR (CDCl$_3$): 1.61-69 (m, 2H, 2×SH), 2.88-2.95 (m, 4H, 2×CH$_2$), 3.41-3.64 (m, 4H, H-3 and H-8), 3.90 and 4.07 (m, 2H, H-2 and H-7).

$^{13}$C-NMR (CDCl$_3$): 28.14-29.11 (CH$_2$), 45.09-45.56 (C(3) and (8)), 60.99-61.96 (C(2) and (7)), 85.55-85.70 (C(5)).

MS: 289 [M+H]$^+$

Method 2

Tetrafluoroboric acid (0.7 mL) was added to a cooled (ice-water), stirred, solution of 2-(mercaptomethyl)-1,3-dithiolane-2-thione (5.70 g; 0.023 moles) of anhydrous dichloromethane (160.0 mL). The resulting mixture, under nitrogen, was treated drop-wise with a solution of mercaptomethylthiirane (3.00 g; 0.028 moles) in anhydrous dichloromethane (60.0 mL). The reaction mixture was allowed to warm to room temperature and stirred for a further 5 hours.

The reaction mixture was treated and washed with water. The organic phase was separated, dried and evaporated to give a yellow oil. Purification by flash-chromatography (10% ethyl acetate in hexane over silica) afforded a diastereoisomeric mixture of 2,7-bis(mercaptomethyl-1,4,6,9-tetrathiaspiro[4.4]nonane as a pale yellow oil (yield 44.7%).

Example 3

Preparation of 2-(S-methyl)-7-vinyl-1,4,6,9-tetrathiaspiro[4.4]nonane Thiolacetate (3)

Tetrafluoroboric acid (0.72 mL) was added to a cooled (ice-water), stirred solution of 2-(S-methyl)-1,3-dithiolane-2-thione thiolacetate (5.01 g; 0.022 moles) in anhydrous dichloromethane (125.0 mL) under nitrogen. The mixture was treated drop-wise, with cooling, with a solution of vinylthiirane (4.66 g; 0.054 moles) in dry dichloromethane (100 mL). The subsequent reaction mixture was allowed to warm to room temperature and stirred for 24 hours.

The reaction mixture was quenched and washed with water. The organic phase was separated, dried and evaporated to yield as a dark brown oil. Purification by flash-chromatography (10% ethyl acetate in hexane over silica) afforded a diastereoisomeric mixture of 2-(S-methyl)-7-vinyl-1,4,6,9-tetrathiaspiro[4.4]nonane thiolacetate as a pale yellow oil (yield 30.3%).

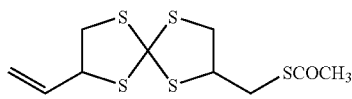

(3)

$^1$H-NMR (CDCl$_3$): 2.36 (s, 3H, CH$_3$), 3.24-3.50 (m, 6H, H-3, H-8, 2×CH$_2$), 4.03 (m, 1H, H-2), 4.50 (m, 1H, H-7), 5.14 (t, 1H, =CH$_2$) and 5.17 (t, 1H, =CH$_2$), 5.91 (m, 1H, —CH=).
$^{13}$C-NMR (CDCl$_3$): 31.05 (CH$_3$), 32.29-33.66 (CH$_2$S), 45.93-47.30 (C(3) and (8)), 57.40-58.54 (C(2)), 61.28-62.27 (C(7)), 85.56-85.62 (C(5)), 117.48-118.95 (=CH$_2$), 134.04-135.44 (—CH=), 194.80-195.17 (CO).
MS: 225 and 311 [M+H]$^+$

Example 4

Preparation of 2-(Mercaptomethyl)-7-vinyl-1,4,6,9-tetrathiaspiro[4.4]nonane (4)

Sodium hydroxide (0.28 g; 0.007 moles) in anhydrous methanol (10.0 mL) was added to a cooled (ice-water) solution of 2-(S-methyl)-7-vinyl-1,4,6,9-tetrathiaspiro[4.4]nonane thiolacetate (2.09 g, 0.007 moles) in dry methanol (10.0 mL). The mixture was allowed to warm to room temperature and left to stir under nitrogen for 22 hours.

The reaction mixture was acidified with 1M aqueous hydrochloric acid and extracted with diethyl ether. The combined diethyl ether extracts were dried and evaporated to yield the diastereoisomeric mixture of 2-(mercaptomethyl)-7-vinyl-1,4,6,9-tetrathiaspiro[4.4]nonane as yellow oil (yield 71.7%).

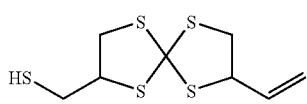

(4)

$^1$H-NMR (CDCl$_3$): 1.65-1.72 (m, 1H, SH), 2.89-2.94 (m, 2H, CH$_2$), 3.30-3.59 (m, 4H, H-3 and H-8), 3.83-4.10 (tm, 1H, H-2), 4.35-4.6 (dm, 1H, H-7), 5.18 (t, 1H, =CH$_2$), 5.33 (m, 1H, =CH$_2$), 5.96 (m, 1H, —CH=).
$^{13}$C-NMR (CDCl$_3$): 28.08-29.04 (CH$_2$S), 45.20-45.71 (C(3)) 46.97-47.37 (C(8)), 60.93-62.35 (C(2) and (7)), 85.49-85.90 (C(5)), 118.24-119.03 (=CH$_2$), 134.03-135.49 (—CH=).
MS: 269 [M+H]$^+$

Example 5

Production of 7-(Mercaptomethyl)-2-(S-methyl)-1,4,6,9-tetrathiaspiro[4.4]nonane Thiolacetate (5)

Tetrafluoroboric acid (0.6 mL) was added to a cooled (ice-water), stirred, solution of 2-(S-methyl)-1,3-dithiolane-2-thione thiolacetate (5.51 g; 0.025 moles) in anhydrous dichloromethane (50.0 mL). The mixture was then treated drop-wise with a solution of vinylthiirane (3.20 g: 0.03 moles) in dry dichloromethane (20.0 mL) under nitrogen. The reaction mixture was allowed to warm to room temperature and stirred for a further 3 hours.

The reaction mixture was quenched with water and the organic layer separated, dried and evaporated to yield a yellow-brown oil. Purification by flash chromatography (10% ethyl acetate in hexane over silica) afforded a diastereoisomeric mixture of 7-(mercaptomethyl)-2-(S-methyl)-1,4,6,9-tetrathiaspiro[4.4]nonane thiolacetate as pale yellow liquid (yield 9.73%).

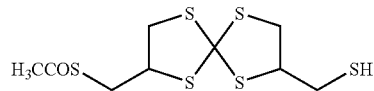

(5)

$^1$H-NMR (CDCl$_3$): 1.68-1.75 (m, 1H, SH), 2.37 (s, 3H, CH$_3$), 2.85-2.98 (m, 2H, CH$_2$SH), 3.24-3.48 (m, 3H, H-3 and CH$_2$SCO), 3.47-3.89 (m, 3H, H-3 and H-8), 3.91 and 4.10 (m, 2H, H-2 and H-7).
$^{13}$C-NMR (CDCl$_3$): 28.3-29.0 (CSH), 30.9 (CH$_3$), 33.5 (CH$_2$SCO), 44.1-45.9 (C(3) and (8)), 57.2-58.0 (C(2)), 60.7-61.7 (C(7)), 85.1-85.5 (C(5)), 194.7-194.9 (CO).
MS: 331 [M+H]$^+$

Example 6

Preparation of 2-Mercaptomethyl-1-oxa-4,6,9-trithiaspiro[4.4]nonane (6a)

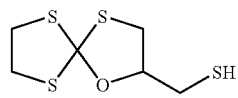

(6a)

A. Preparation of 2-(S-methyl)-1-oxa-4,6,9-trithiaspiro[4.4]nonane Thiolacetate (6b)

2-(Chloromethyl-1-oxa-4,6,9-trithiaspiro[4.4]nonane (3.50 g; 0.015 mol) in anhydrous DMF (10.0 mL) was added drop-wise, over a period of 30 minutes, to a stirred solution of potassium thiolacetate (8.73 g; 0.077 mol) in anhydrous DMF (36.5 mL) under nitrogen. The mixture was stirred at room temperature for 16 hours.

The reaction mixture was evaporated and the residue dissolved in chloroform and washed twice with water. The organic phase was separated, dried and evaporated to yield a brown oil. Purification by flash chromatography (toluene over silica) afforded 2-(S-methyl)-1-oxa-4,6,9-trithiaspiro[4.4]nonane thiolacetate as a yellow oil (3.19 g; 77.60% yield).

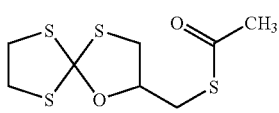
(6b)

$^{1}$H-NMR (CDCl$_{3}$): 2.37 (s, 3H, CH$_{3}$), 2.97 (dd, 1H, H-3), 3.18 (dd, 1H, H-3), 3.31 (m, 2H, CH$_{2}$S), 3.38 (m, 2H, H-7 or 8), 3.52 (m, 2H, H-7 or 8), 4.37 (m, 1H, H-2).
$^{13}$C-NMR (CDCl$_{3}$): 30.87 (CH$_{3}$), 31.19 (CH$_{2}$), 38.22 (C(3)), 41.12 (C(7 or 8)), 42.21 (C(7 or 8)), 82.74 (C(2)), 113.20 (C(5)), 195.03 (C=O).

B. Preparation of 2-(Mercaptomethyl)-1-oxa-4,6,9-trithiaspiro[4.4]nonane (6c)

2-(S-methyl)-1-oxa-4,6,9-trithiaspiro[4.4]nonane thiolacetate (2.75 g; 0.010 mol) in anhydrous THF (20.0 mL) was added drop-wise to a sired, cooled (–10° C.), solution of 1.0M lithium aluminum hydride (30.75 mL; 0.031 mol) in THF under nitrogen. The resulting mixture was stirred for 30 minutes then allowed to warm to room temperature and stirred for a further 15 hours.

The reaction mixture was acidified to pH 4 with 10% aqueous sulfuric acid and extracted with diethyl ether. The organic portion was separated, dried and evaporated to yield 2-(mercaptomethyl)-1-oxa-4,6,9-trithiaspiro[4.4]nonane as a pale yellow oil (2.05 g; 0.009 mol, 88.4% yield).

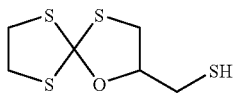
(6c)

$^{1}$H-NMR (CDCl$_{3}$): 1.65 (s, 1H, SH), 2.84 (m, 1H, CH$_{2}$S), 2.95 (m, 1H, CH$_{2}$S), 3.10 (m, 1H, H-3), 3.26 (m, 1H, H-3), 3.39 (m, 2H, H-7 or 8), 3.53 (m, 2H, H-7 or 8), 4.37 (m, 1H, H-2).
$^{13}$C-NMR (CDCl$_{3}$): 27.08 (CH$_{2}$), 38.09 (C(3)), 41.21 (C(7 or 8)), 42.22 (C(7 or 8)), 85.07 (C(2)), 113.34 (C(5)).

Preparation of BisSTOCS and BisSOTOCS

Example 7

To prepare bisSTOCs according to the reaction, a substituted or unsubstituted ethylenetrithiocarbonate will be reacted with bis-methylthiirane sulphide (n=1) or bis-methylthiirane disulphide (n=2), in the presence of a catalytic amount of tetrafluoroboric acid.

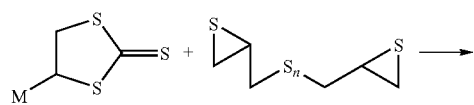

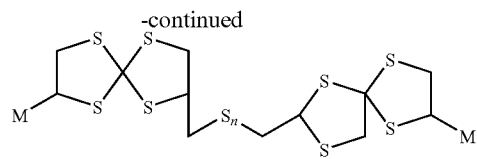

Preferably M is =CR$_{2}$SR', CR$_{2}$=CH$_{2}$, wherein R=H, C$_{1}$-C$_{4}$ alkyl, R'=H, acetyl, allyl, acrylate, or methacrylate); and
n=1 or 2.

Preparation of 2,2'-[thiobis(methylene)]bis-1,4,6,9-tetrathiaspiro[4.4]nonane (7')

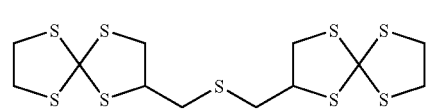
(7')

A mixture of ethylene trithiocarbonate (5.04 g, 0.037 moles) and tetrafluoroboric acid (1.0 ml) in anhydrous dichloromethane (50.0 ml) cooled to –5° C. and stirred under nitrogen, was treated dropwise with a solution of 2,2'-[thiobis (methylene)]bis-thiirane (3.34 g, 0.019 moles) in anhydrous dichloromethane (30.0 ml). The resulting mire was allowed to warm to room temperature and quenched with 5% sodium bicarbonate solution (50.0 ml). The separation of the organic layer followed by water washing, drying and evaporation afford a wet yellow solid. Purification of which by short-path chromatography (20% ethyl acetate/hexane over silica) afforded 2,2'-[thiobis(methylene)]bis-1,4,6,9-tetrathiaspiro[4.4]nonane (4.7% yield).
$^{1}$H-NMR (CDCl$_{3}$): 2.90-3.50 (m, 16H, 2×CH$_{2}$ and H-3, 3', 7, 7', 8 and 8'), 4.00 (m, 2H, H-2 and 2').
$^{13}$C-NMR (CDCl$_{3}$): 36.0 (2×CH$_{2}$), 39.52-42.56 (C(7, 7', 8 and 8')), 45.86 (C(3 and 3')), 58.23 (C(2 and 2')), 85.73 (C(5 and 5')).

Example 8

Preparation of 2,7-Bis(mercaptomethyl)-1-oxa-4,6,9-trithiaspiro[4.4]nonane (7a)

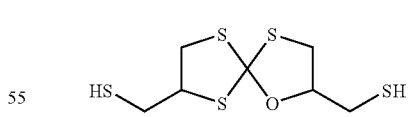
(7a)

A. Preparation of 2-(Chloromethyl)-7-(S-methyl)-1-oxa-4,6,9-trithiaspiro[4.4]nonane Thiolacetate (7b)

Tetrafluoroboric acid (2.1 mL) was slowly added to a stirred, cooled (–10° C.) solution of 4-(S-methyl)-1,3-dithiolane-2-thione thiolacetate (18.50 g; 0.082 mol) in anhydrous dichloromethane (400 mL) under nitrogen. The resulting cooled mixture was treated dropwise with a solution of epichlorohydrin (16.91 g; 14.29 mL, 0.183 mol) in anhydrous dichloromethane (50.0 mL). The reaction mixture was allowed to warm to room temperature and stirred overnight.

The reaction mixture was washed twice with water and the organic phase separated, dried and evaporated to yield a dark yellow oil (29.44 g). Purification by flash-chromatography (20% ethyl acetate in hexane over silica) yielded 2-(chloromethyl)-7-(S-methyl)-1-oxa-4,6,9-trithiaspiro[4.4]nonane thiolacetate (76) (7.55 g; 28.89% yield) as an off-white oil.

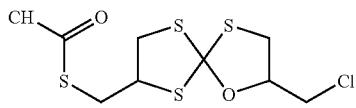
(7b)

$^1$H-NMR (CDCl$_3$): 2.36 (s, 3H, CH$_3$), 3.11 (m, 1H, H-3), 3.28-3.60 (m, 5H, H-3, H-8, CH$_2$S), 3.75 (m, 2H, CH$_2$Cl), 4.00 and 4.15 (m, 1H, H-7), 4.50 (m, 1H, H-2).

$^{13}$C-NMR (CDCl$_3$): 30.95 (CH$_3$), 32.95-34.02 (CH$_2$S), 37.37-37.56 (C(3)), 43.59-43.81 (CH$_2$Cl), 44.19-45.67 (C(8)), 57.05-59.05 (C(7)), 82.83-83.31 (C(2)), 113.11-114.09 (C(5)), 194.92-195.38 (C=O).

B. Preparation of 2,7-Bis(S-methyl)-1-oxa-4,6,9-trithiaspiro[4.4]nonane Thiolacetate (7c)

2-(Chloromethyl)-7-(S-methyl)-1-oxa-4,6,9-trithiaspiro[4.4]nonane thiolacetate (7.00 g; 0.022 mol) in anhydrous DMF (40.0 mL) was added over 30 minutes to a stirred solution of potassium thiolacetate (3.53 g; 0.031 mol) in anhydrous DMF (70.0 mL). The reaction was left to stir at room temperature under nitrogen for 20 hours The resulting reaction mixture was evaporated and the residue dissolved in chloroform and washed twice with water. The organic phase was separated, dried and evaporated to yield a dark yellow oil. Purification by chromatography (toluene over flash-silica) yielded 2,7-bis(S-methyl)-1-oxa-4,6,9-trithiaspiro[4.4]nonane thiolacetate as dark yellow oil (3.86 g; 35.00% yield).

(7c)

$^1$H-NMR (CDCl$_3$): 2.37 (m, 6H, CH$_3$ and CH$_3$), 2.95 (m, 1H, H-3), 3.15-3.75 (m, 7H, H-3, H-8, CH$_2$S and CH$_2$S), 3.95-4.25 (m, 1H, H-7), 4.35 (m, 1H, H-2).

$^{13}$C-NMR (CDCl$_3$): 30.48-30.80 (CH$_3$ and CH$_3$), 32.11-33.73 (CH$_2$S and CH$_2$S), 37.72-37.92 (C(3)), 43.78-45.34 (C(8)), 56.54-58.68 (C(7)), 82.23-82.61 (C(2)), 112.27-113.18 (C(5)), 194.58-195.09 (C=O).

C. Preparation of 2,7-Bis(mercaptomethyl)-1-oxa-4,6,9-trithiaspiro[4.4]nonane (7a)

2,7-Bis(S-methyl)-1-oxa-4,6,9-trithiaspiro[4.4]nonane thiolacetate (3.39 g; 0.095 mol) in anhydrous THF (20.0 mL) was added drop-wise to a stirred cooled (−10° C.) solution of 1.0M lithium aluminum hydride (28.52 ml; 0.029 mol) in THF under nitrogen. The resulting mixture was stirred for 30 minutes and then allowed to warm to room temperature and then stirred for a further 18 hours.

The reaction mixture was acidified to pH 4 with 10% sulfuric acid and extracted with diethyl ether. The organic portion was separated, dried and evaporated to give a brown oil. Purification by vacuum distillation (92-94° C./0.15 mmHg) afforded 2,7-bis(mercaptomethyl)-1-oxa-4,6,9-trithiaspiro[4.4]nonane as a pale yellow oil (0.25 g; 3.2% yield).

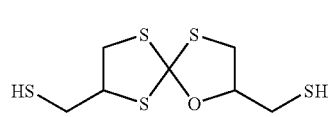
(7a)

$^1$H-NMR (CDCl$_3$): 1.65-1.75 (m, 2H, SH and SH), 2.77-3.75 (m, 8H, H-3, H-8, CH$_2$S and CH$_2$S), 3.93 and 4.20 (m, 1H, H-7), 4.36 (m, 1H, H-2).

$^{13}$C-NMR (CDCl$_3$): 28.01-33.08 (CH$_2$ & CH$_2$), 38.99-39.19 (C(3)), 43.98-46.07 (C(8)), 61.39-53.67 (C(7)), 85.79-86.27 (C(2)), 113.61-114.53 (C(5)).

Example 9

Preparation of a bisSTOC

Bis-ethylenetrithiocarbonate sulfide (n=1) or bis-ethylenetrithiocarbonate (n=2), will be reacted with substituted thiirane (5), in the presence of a catalytic amount of tetrafluoroboric acid to yield a bisSTOC.

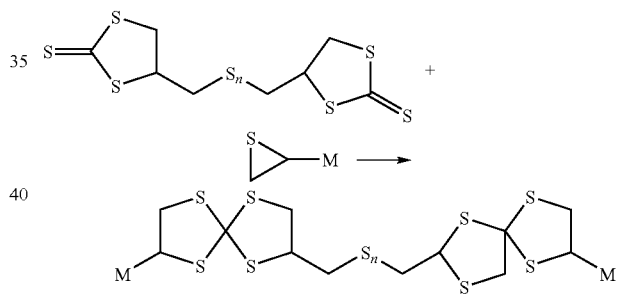

wherein M is CR$_2$Cl, CR$_2$SR', CR$_2$=CH$_2$,
R=H, C$_1$-C$_4$ alkyl;
R'=H, allyl, acrylate, or methacrylate; and
n=1 or 2.

Example 10

Preparation of a bisSOTOC

Substituted ethylenedithiocarbonates will be reacted with bis-methylthiirane sulphide (n=1), or bis-methylthiirane disulphide (n=2) in the presence of a catalytic amount of tetrafluoroboric acid to yield a bisSOTOC:

wherein M=CR$_2$SR', CR$_2$=CH$_2$;

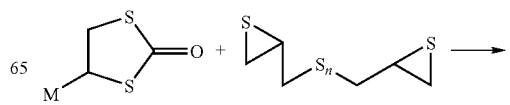

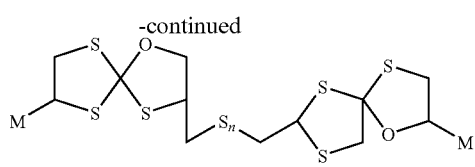

R=H, $C_1$-$C_4$ alkyl;
R'=H, acetyl, allyl, acrylate, methacrylate; and
n=1 or 2.

Example 11

Preparation of a bisSOTOC

Bis-ethylenetrithiocarbonate sulfide (n=1), or bis-ethylenetrithiocarbonate (n=2) will be reacted with substitute oxirane in the presence of a catalytic amount of tetrafluoroboric acid to yield a bisSOTOC.

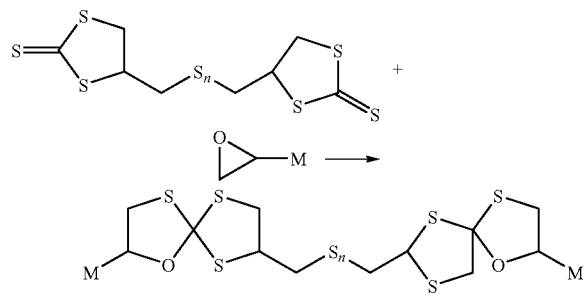

wherein M is =$CR_2Cl$, $CR_2OR'$, $CR_2$=$CH_2$,
R=H, $C_1$-$C_4$ alkyl;
R'=H, allyl, acrylate, or methacrylate; and
n=1 or 2.

Methods of Polymerizing and Using STOCS, SOTOCS BisSTOCS and BisSOTOCS

Each STOC, SOTOC, bisSTOC or bisSOTOC compound, or a mixture thereof, having at least one, preferably 2 SH bearing substituent(s), may be reacted with at least one polyisocyanate (or prepolymer thereof), preferably a diisocyanate such as an aromatic diisocyanate, to form a polythiourethane polymer having a high refractive index.

Each STOC, SOTOC, bisSTOC or bisSOTOC compound, or a mixture thereof, having at least one, preferably 2 SH bearing substituent(s), may be reacted with a monomer having at least one unsaturated reactive group, such as a vinyl group, an allyl group, a (meth)acryl group or a thio(meth)acryl group and/or a mixture of such monomers and/or one or more polyepisulfide(s) to form a polymer having a high refractive index, especially a polysulfide polymer.

Each STOC, SOTOC, bisSTOC or bisSOTOC compound, or a mixture thereof, having at least one preferably 2 episulfide bearing substituent(s), may be reacted with a monomer having at least one, preferably 2 SH group(s) or a mixture of such monomers and/or one or more polyepisulfide(s) to form a polymer having a high refractive index, especially a polysulfide polymer.

Each STOC, SOTOC, bisSTOC or bisSOTOC compound bearing at least one unsaturated group such as vinyl group or a (meth)acryl group can be reacted with one or more copolymerisable monomers such as monomer(s) having at least one unsaturated group such as those recited above and/or with one or more polythiol monomers and/or with one or more polyepisulfide monomers (or prepolymers thereof) in order to prepare a polymer having a high refractive index.

Polymerization and copolymerization of the STOCs, SOTOCs, bisSTOCs and bisSOTOCs compounds of the invention is generally carried out in the presence of a polymerization in the usual proportions. A preferred (co)polymerization catalyst comprises an effective amount of at least one salt of formula:

$$M_M^{P+}Y_n^-$$

wherein $M^{P+}$ is a cation selected from the group consisting of alkaline metals, alkaline earth metals, transitions metals and ammonium groups of formula $NR^+_4$ in which R is an alkyl radical, $Y^-$ is an anion such as the corresponding acid YH has a pKa fulfilling the condition 0.5 .pKa. 14 with the proviso that when the mixture comprises an episulfide compound and $M^{P+}$ is an ammonium group, the mixture also comprises an electro-donor compound, p is the valency of the cation, and
n=mxp.

Another preferred (co)polymerization catalyst for copolymerization of compounds of the invention having polythiol groups and polyisocyanates is a tin catalyst such as dibutyltindichloride.

Example 12

Preparing a Polythiourethane from a STOC

The disulfide 2,7 bis(mercaptomethyl-1,4,6,9-tetrathiospiro[4.4]nonane of Example 2 can be used to make polythiourethanes, via reaction with diisocyanates. A mixture of 2,7 bis(mercaptomethyl)-1,4,6,9-tetrathiospiro[4.4] nonane, xyl.ylenediisocyante (mol NCO/mol SH=1.0) and dibutyltin dilaurate (mol Sn/mol SH=$10^{-4}$) is homogeneously stirred, injected into a glass mold assembly, and polymerized at 60° C. for 15 hours then at 120° C. for 3 hours. The obtained lens is optically clear with a high refractive index and may be expected to show better mechanical and heat resistance properties than present in prior polythiourethanes.

Example 13

Preparation of an m-XDI/[4.4] STOC Based Polymer

A mixture of m-xylylene diisocyanate (m-XDI) and 2,7-Bis(mercaptomethyl)-1,4,6,9-tetrathiaspiro[4.4]nonane ([4.4] STOC) is stirred magnetically in a glass vial at room temperature. A catalyst solution prepared from 0.3434 g KSCN, 1.3979 g (18.6) Crown ether and 2.2659 g 2-mercaptoethanol is added to the mixture, which is then stirred and cured in an oven from 20. C to 90. C for 2 hrs and then at 150. C for 2 hrs.

Example 14

Preparation of an m-XDI/[4.4] STOC Based Polymer $SnBu_2Cl_2$ is dissolved in m-XDI at room temperature, then added together with [4.4] STOC and stirred magnetically prior to curing at 30. C for 6 hrs, then 30. C to 60. C for 3 hrs, then 60. C for 1 hr, 60. C to 80. C for 2 hrs, 80. C for 4 hrs, 80. C to 150. C for 3 hrs, 150. C for 1 hr, 150. C to 75. C for 2.5 hrs. The experimental conditions and the results of these experiments are summarized in Table 3.

TABLE 3 m-XDI/[4.4] STOC based polymers

|  | Ex. 1 | Ex. 2 |
|---|---|---|
| m-XDI (g)[a)] | 0.6541 | 0.6525 |
| [4.4] STOC (g) | 0.9998 | 0.9932 |
| Mol SH/mol NCO | 0.997 | 0.993 |
| Catalyst | KSCN solution[b)] | SnBu$_2$Cl$_2$ |
| Catalyst (g) | 6.3 × 10$^{-4}$ | 1.7 × 10$^{-4}$ |
| Cure cycle | c) | d) |
| Glass Transition Temperature (.C.)[e)] | 100 | 102 |
| Refractive Index (ne) | 1.692 | 1.693 |
| Abbe number (ve) | 31 | 31 |
| Density | 1.437 | 1.436 |

[a)]m-Xylylene diisocyanate
[b)]Made from 0.3434 g KSCN + 1.3979 g (18.6) Crown ether + 2.2659 g 2-mercaptoethanol
c) 20. C. to 90. C. (2 hrs) + 150. C. (2 hrs)
d) 30. C. (6 hrs), 30. C. to 60. C. (3 hrs), 60. C. (1 hr), 60. C. to 80. C. (2 hrs), 80. C. (4 hrs), 80. C. to 150. C. (3 hrs), 150. C. (1 hr), 150. C. to 75. C. (2.5 hrs).
[e)]Measured by Differential Scanning Calorimetry After testing, the [4.4] STOC monomers successfully reacted with m-XDI to produce transparent high index polymers.

Example 15

Preparing a Vinyl Functionalized STOC and Its Polymer

Another method of polymerizing 2,7-bis(mercaptomethyl)-1,4,6,9-tetrathiospiro[4.4]nonane of Example 2 is to convert its SH groups into S—CH=CH2 groups by reaction with sodium ethoxide in ethanol, followed by a reaction with vinylbromide. The resulting 2,7-bis(2-thia-3-butenyl)-1,4,6,9-tetrathiospiro[4.4]nonane could be polymerized by mixing it with a radical initiator (such as 2,2'-azobis(2,4-dimethyl-valeronitrile), 1% w/w) and heating the mixture to 120° C. for 21 hours. This polythiourethane will have high index and may be expected to show better impact properties than prior thiourethanes.

Example 16

Preparing a Methacrylate Functionalized STOC and its Polymer

Another way of polymerizing 2,7 bis(mercaptomethyl)-1,4,6,9-tetrathiospiro[4.4]nonane of Example 2 is to convert its SH groups into thiomethacrylate groups by reaction with methacrylic anhydride in the presence of a mixture of an aqueous solution of sodium hydroxide, methyl ter-butyl ether and 2,6-di-ter-butyl-methyl phenol. The resulting dithiomethacrylate monomer could be polymerized by UV light in the presence of a radical photoinitiator (such as methyl phenylglycoxylate, 1% w/w), or by heat in the presence of a heat curing initiator (such as 2,2'-azobisisobutyronitrile, 1% w/w).

This polythiourethane will have high index and may be expected to show better impact properties than prior thiourethanes.

Example 17

Preparing a Polythiourethane from a SOTOC

The oxygen containing version of the compound used in Examples 12, 15 and 16, i.e., 2,7-bis(mercaptomethyl)-1-oxa-4,6,9-trithiaspiro[4.4]nonane, can also be used to make high index thiourethanes with similar properties. Any related compounds, including 3,7,-bis(mercaptomethyl)-1-oxa-4,6,9-trithiaspiro[4.4]nonane, may also be used in this manner. Additionally, dithiaspiro compounds such as: 2,7,-bis(mercaptomethyl)-1,4-oxa-6,9-dithiaspiro[4.4]nonane, 3,8-bis(mercaptomethyl)-1,6-oxa-4,9-dithiaspiro[4.4]nonane, 3,7,-bis(mercaptomethyl)-1,6-oxa-4,9-dithiaspiro[4.4]nonane, and 2,7,-bis(mercaptomethyl)-1,6-oxa-4,9-dithiaspiro[4.4]nonane, may also be polymerized in this manner.

It should be noted that isomeric oxatrithiaspiro species may be achieved by causing a three membered oxirane to transition through a much more unstable/higher energy species or, alternatively, via a reaction scheme that uses a staring material having oxygen atoms appropriately positioned in the 5-membered rings, e.g., as with ethylenedithiocarbonate. Without being bound to any specific theory, it is believed that The isomeric oxatrithia derivative may very well be produced in the common reaction, albeit in small amounts.

In another example, the monothio compounds described above, such as, 2-(mercaptomethyl)-1,4,6,9-tetrathiospiro[4.4]nonane, as shown in Example 1, can be used to prepare thioacrylate compounds with useful properties. Likewise, trithiaspiro compounds, including the 2-mercaptomethyl-1-oxa-4,6,9,-trithiaspiro[4.4]nonane, as shown in above and related trithiaspiro compounds such as 3-mercaptomethyl-1-oxa-4,6,9-trithiaspiro[4.4]nonane, 6-mercaptomethyl-1-oxa-4,6,9-trithiaspiro[4.4]nonane, may be used in this manner. Further, dithiaspiro compounds such as: 2-mercaptomethyl-1,4-oxa-6,9-dithiaspiro[4.4]nonane, 2-mercaptomethyl-1,6-oxa-4,9-dithiaspiro[4.4]nonane, and 3-mercaptomethyl-1,6-oxa-4,9-dithiaspiro[4.4]nonane, may be used to prepare thioacrylates in this manner. Of course, the above described methods of polymerization, and the compounds employed therein are all subject to modification and expansion by those of ordinary skill, in view of the disclosure herein.

Example 18

Methods of Forming Lenses from Polymers of STOCs and/or SOTOCs or the Bis Compounds Those of ordinary skill will be able to use the methods described, e.g., in Example 12, and the compositions described elsewhere in the specification to prepare lenses in any number of ways. For example, these compounds may be polymerized in a mold to form a lens or lens blank. Further, these compounds may be polymerized and then ground or otherwise machined into a finished lens. Lenses thus formed may receive any number of abrasion resistant, antireflective, intact resistant, or other coatings to reach their final form. These lenses may be used in any suitable manner.

What is claimed is:

1. A compound of Formula I:

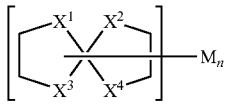

or Formula II:

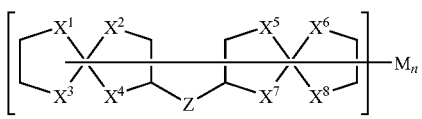

wherein $X^1$, $X^2$, $X^3$, $X^4$, $X^5$, $X^6$, $X^7$ and $X^8$ are independently O or S; and in compound of formula I at least two and up to all four of $X^1$, $X^2$, $X^3$ and $X^4$ are sulfur;

Z is —$C_mR^2_{2m}$— wherein m=1 to 4; —$C(R^2)_2SC(R^2)_2$—, —$C(R^2)_2SSC(R^2)_2$—, or —$C(R^2)_2OC(R^2)_2$;

n is 1 to 4 in compound of formula I and is 0 to 4 in compound of formula II;

M is selected from $CH_2Cl$, $CH_2SC(O)R^1$, $CH_2SC(S)R^1$, $CH_2S(CH_2CH_2S)_qH$ wherein q is 0, 1 or 2; —$CR^2$=$CH_2$, —$CH_2OC(O)CR^2$=$CH_2$, $CH_2N$=$C$=$S$, $CH_2N$=$C$=$O$, $CH_2NR^2H$, $CH_2OH$, $CH_2SCH_2CH_2CR^2$=$CH_2$, phenyl, $C(R^2)_2$ phenyl, furan, thiophene, halogen, $C_3$-$C_6$ cycloalkyl, $C_3$-$C_6$ heretocyclics, thiol,

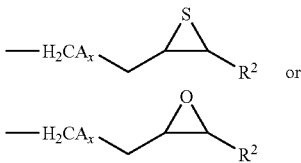

A is O, S or phenyl and x is 0 or 1;

wherein $R^1$ is $C_1$-$C_{22}$ alkyl; and $R^2$ is H or $C_1$-$C_{22}$ alkyl.

2. The compound of claim 1, wherein in the compound of formula II at least two and up to all four of $X^1$, $X^2$, $X^3$ and $X^4$, and at least two and up to all four of $X^5$, $X^6$, $X^7$, and $X^8$ are sulfur.

3. The compound of claim 1, further defined as having Formula II:

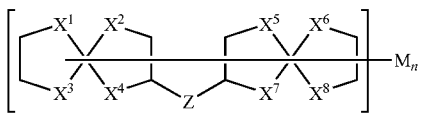

wherein n is 1, 2, 3 or 4.

4. The compound of claim 1, further defined as:
2-(Mercaptomethyl)-1,4,6,9-tetrathiaspiro[4.4]nonane;
2,7-Bis(mercaptomethyl)-1,4,6,9-tetrathiaspiro[4.4]nonane;
2-(S-methyl)-7-vinyl-1,4,6,9-tetrathiaspiro[4.4]nonane thiolacetate;
2-(Mercaptomethyl)-7-vinyl-1,4,6,9-tetrathiaspiro[4.4]nonane;
7-(Mercaptomethyl)-2-(S-methyl)-1,4,6,9-tetrathiaspiro[4.4]nonane thiolacetate;
2-Mercaptomethyl-1-oxa-4,6,9-trithiaspiro[4.4]nonane; or
2,7-Bis(mercaptomethyl)-1-oxa-4,6,9-trithiaspiro[4.4]nonane.

5. The compound of claim 1, further defined as:
2-(Chloromethyl)-1,4,6,9-tetrathiaspiro[4.4]nonane;
2-(S-Methyl)-1,4,6,9-tetrathiaspiro[4.4]nonane thiolacetate;
4-(S-Methyl)-1,3-dithiolane-2-thione thiolacetate;
2-(Chloromethyl)-7-(S-methyl)-1,4,6,9-tetrathiaspiro[4.4]nonane thiolacetate;
2,7-Bis(S-methyl)-1,4,6,9-tetrathiaspiro[4.4]nonane thiolacetate;
2-(S-methyl)-1-oxa-4,6,9-trithiaspiro[4.4]nonane thiolacetate;
2-(Mercaptomethyl)-1-oxa-4,6,9-trithiaspiro[4.4]nonane;
2-(Chloromethyl)-7-(S-methyl)-1-oxa-4,6,9-trithiaspiro[4.4]nonane thiolacetate; or
2,7-Bis(S-methyl)-1-oxa-4,6,9-trithiaspiro[4.4]nonane thiolacetate.

6. A method for manufacturing optical lenses comprising:
polymerizing a compound of Formula I:

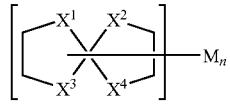

or a compound of Formula II:

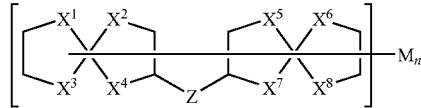

wherein $X^1$, $X^2$, $X^3$, $X^4$, $X^5$, $X^6$, $X^7$ and $X^8$, are independently O or S; and in compound of formula I at least two and up to all four $X^1$, $X^2$, $X^3$ and $X^4$ are sulfur;

Z is —$C_mR^2_{2m}$— wherein m=1-4; —$C(R^2)_2SC(R^2)_2$—, —$C(R^2)_2SSC(R^2)_2$—, or —$C(R^2)_2OC(R^2)_2$;

n is 1 to 4 in compound of formula I and is from 0 to 4 in compound of formula II; and M is selected from $CH_2Cl$, $CH_2SC(O)R^1$, $CH_2SC(S)R^1$, $CH_2S(CH_2CH_2S)qH$ wherein q is 0, 1 or 2, —$CR^2$=$CH_2$, —$CH_2OC(O)CR^2$=$CH_2$, $CH_2N$=$C$=$S$, $CH_2N$=$C$=$O$, $CH_2NR^2H$, $CH_2OH$, $CH_2SCH_2CH_2CR^2$=$CH_2$, phenyl, $C(R^2)_2$ phenyl, furan, thiophene, halogen, $C_3$-$C_6$ cycloalkyl, $C_3$-$C_6$ heretocyclics, thiol,

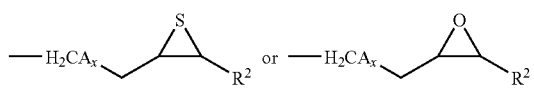

wherein A is S, O or phenyl and x is 0 or 1;

$R^1$ is $C_1$-$C_{22}$ alkyl; and $R^2$ is H or $C_1$-$C_{22}$ alkyl to form a polymer, forming all or part of the optical lens.

7. The method of claim 6, wherein in compound of formula II at least two and up to all four of $X^1$, $X^2$, $X^3$ and $X^4$ and at least two and up to all four of four of $X^5$, $X^6$, $X^7$, and $X^8$ are sulfur.

8. The method of claim 6, wherein the polymer forms a body of the lens.

9. The method of claim 6, wherein the polymer forms a coating of the lens.

10. A (co)polymer comprising (co)polymerized monomers of Formula I:

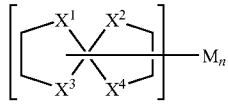

or Formula II:

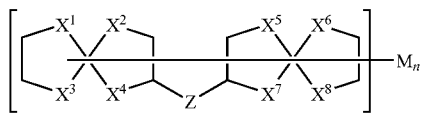

wherein $X^1$, $X^2$, $X^3$, $X^4$, $X^5$, $X^6$, $X^7$, and $X^8$, are independently O or S; and in compound of formula I at least two and up to all four $X^1$, $X^2$, $X^3$ and $X^4$ are sulfur, Z is $-C_mR^2{}_{2m}-$ wherein m=1-4; $-C(R^2)_2SC(R^2)_2-$, $-C(R^2)_2SSC(R^2)_2-$, or $-C(R^2)_2OC(R^2)_2$;

n is from 1 to 4 in compound of formula I and n is 0 to 4 in compound of formula II; and M is selected from $CH_2Cl$, $CH_2SC(O)R^1$, $CH_2SC(S)R^1$, $CH_2S(CH_2CH_2S)qH$ wherein q is 0, 1 or 2; $-CR^2=CH_2$, $-CH_2OC(O)CR^2=CH_2$, $CH_2N=C=S$, $CH_2N=C=O$, $CH_2NR^2H$, $CH_2OH$, $CH_2SCH_2CH_2CR^2=CH_2$, phenyl, $C(R^2)_2$ phenyl, furan, thiophene, halogen, $C_3$-$C_6$ cycloalkyl, $C_3$-$C_6$ heterocyclics, thiol;

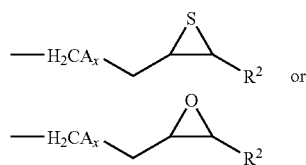

wherein A is S, O or phenyl and x is 0 or 1;

$R^1$ is $C_1$-$C_{22}$ alkyl; and $R^2$ is H or $C_1$-$C_{22}$ alkyl.

11. The (co)polymer of claim 10, wherein in compound of formula II at least two and up to all four of $X^1$, $X^2$, $X^3$ and $X^4$ and at least two and up to all four of $X^5$, $X^6$, $X^7$ and $X^8$ are sulfur.

12. The (co)polymer of claim 10, further defined as comprised in an optical lens.

13. A method for preparing a bis-derivative of a spirotetrathiocarbonate or spirooxothiocarbonate, comprising using either one of the following reactions schemes:

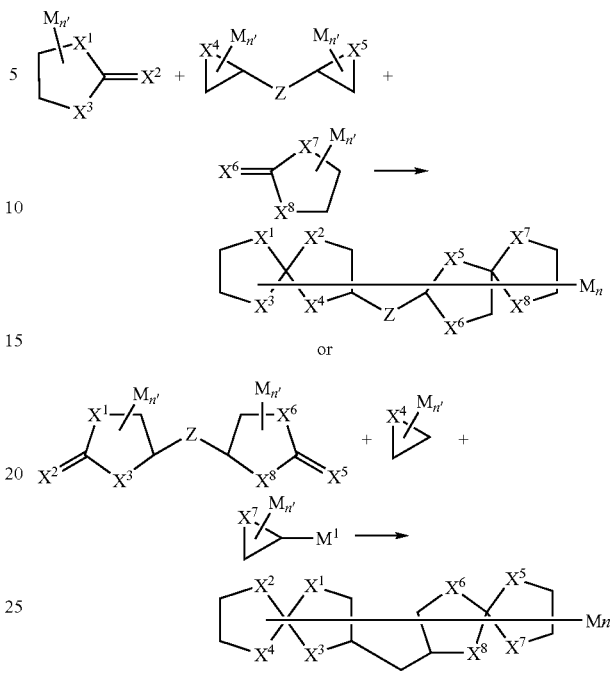

wherein $X^1$, $X^2$, $X^3$, $X^4$, $X^5$, $X^6$, $X^7$, and $X^8$ are independently O or S; n' is independently 0, 1 or 2;

n is 0 to 4,

Z is $-C_mR^2{}_{2m}-$ wherein m=1-4; $-C(R^2)_2SC(R^2)_2-$, $-C(R^2)_2SSC(R^2)_2-$, $-C(R^2)_2OC(R^2)_2-$;

M is independently selected from $CH_2Cl$, $CH_2SH$, $CH_2SC(O)R^1$, $CH_2SC(S)R^1$, $CH_2S(CH_2CH_2S)qH$ wherein q is 0, 1 or 2, $-CR^2=CH_2$, $-CH_2OC(O)CR^2=CH_2$, $CH_2N=C=S$, $CH_2N=C=O$, $CH_2NR^2H$, $CH_2OH$, $CH_2SCH_2CH_2CR^2=CH_2$, phenyl, $C(R^2)_2$ phenyl, furan, thiophene, halogen, $C_3$-$C_6$ cycloalkyl, $C_3$-$C_6$ heterocyclics, thiol,

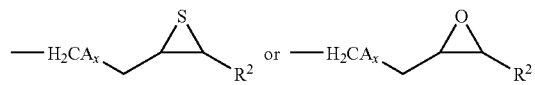

wherein A is S, O or phenyl and x is 0 or 1;

$R^1$ is $C_1$-$C_{22}$ alkyl; and $R^2$ is H or $C_1$-$C_{22}$ alkyl.

14. The method of claim 13, comprising reacting a substituted ethylenetrithiocarbonate with a bis-methylthiirane sulfide or a bis-methylthiirane disulfide, in the presence of a catalytic amount of tetrafluoroboric acid to produce the bis-STOC as shown in the reaction below:

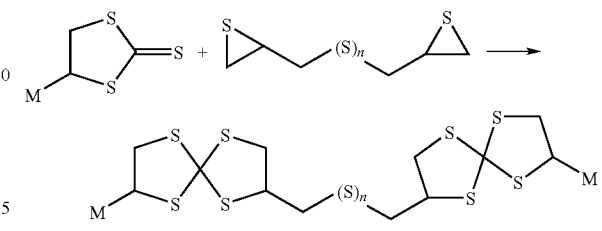

wherein M is selected from $CR_2SR'$, $CR_2=CH_2$,
R=H, $C_1$-$C_4$ alkyl; and
R'=H, acetyl, allyl, acrylate, or methacrylate and
n=1 or 2.

15. The method of claim 13, comprising reacting a bis-ethylenetrithiocarbonate sulfide or a bis-ethylenetrithiocarbonate, with substituted thiirane in the presence of a catalytic amount of tetrafluoroboric acid to produce the bisSTOC according to the following reaction:

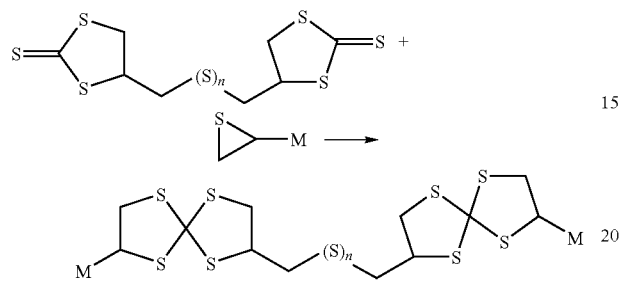

wherein M is $CR_2Cl$, $CR_2SR'$, or $CR_2=CH_2$,
R is H, $C_1$-$C_4$ alkyl,
R' is H, allyl, acrylate, or methacrylate and
n=1 or 2.

16. The method of claim 13, comprising reacting a substituted ethylenedithiocarbonate with bis-methylthiirane sulfide or bis-methylthiirane disulfide in the presence of a catalytic amount of tetrafluoroboric acid to produce the compound of formula II according to the reaction:

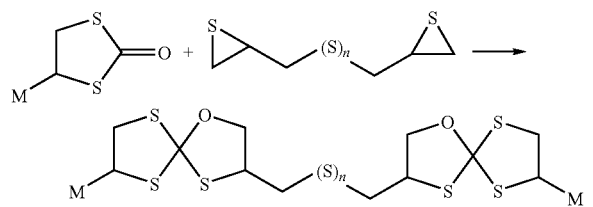

wherein M=$CR_2SR'$, $CR_2=CH_2$;
R=H, $C_1$-$C_4$ alkyl;
R'=H, acetyl, allyl, acrylate, or methacrylate; and
n=1 or 2.

17. The method of claim 13, further defined as a method wherein at least one of bis-ethylenetrithiocarbonate sulfide or bis-ethylenetrithiocarbonate is reacted with a substituted oxirane, in the presence of a catalytic amount of tetrafluoroboric acid to produce the compound of formula II according to the reaction:

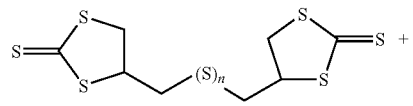

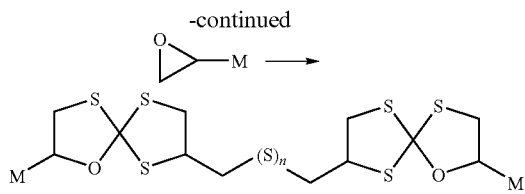

wherein M=$CR_2Cl$, $CR_2OR'$ or $CR_2=CH_2$;
R=H, $C_1$-$C_4$ alkyl;
R'=H, allyl, acrylate or methacrylate; and
n=1 or 2.

18. A method of preparing a polythiourethane polymer having a refractive index of 1.5 or greater, comprising reacting at least one polyisocyanate or prepolymer thereof with a compound having formula I or II in claim 1 or a mixture thereof, wherein said compound is further defined as having at least one SH bearing substituent.

19. The method of claim 18, wherein the at least one polyisocyanate or prepolymer thereof is a diisocyanate or prepolymer thereof.

20. The method of claim 18, wherein compound of formula I or formula II has at least two SH bearing substituents.

21. The method of claim 18, further defined as comprising:
preparing a mixture of m-xylylene diisocyanate (m-XDI) and 2,7 bis(mercaptomethyl)-1,4,6,9-tetrathiaspiro[4.4] nonane;
adding a catalyst solution comprising KSCN and a crown-ether; and
curing the mixture at a temperature above 20° C.

22. The method of claim 18, further defined as comprising:
Dissolving $SnBu_2Cl_2$ in m-xylene diisocyanate (m-XDI);
adding 2,7-bis(mercaptomethyl)-1,4,6,9-tetrathiaspiro [4.4] nonane;
stirring; and
curing at a temperature above 30° C.

23. A method of preparing a polymer having a high refractive index which comprises reacting a monomer having at least one unsaturated reactive group or a mixture thereof and/or one or more polyepisulfides with a compound of formula I or formula II of claim 1 having at least one SH bearing substituent(s) or a mixture thereof.

24. The method of claim 23, wherein the compound of formula I or formula II has at least two SH bearing substituents.

25. A method of preparing a polymer having a high refractive index which comprises reacting a monomer having at least one SH group or a mixture thereof and/or one or more polyepisulfides with a compound of formula I or of formula II of claim 1 having at least one, preferably two episulfide bearing substituent(s) or a mixture thereof.

26. The method of claim 25, wherein the monomer has at least two SH groups.

\* \* \* \* \*

UNITED STATES PATENT AND TRADEMARK OFFICE
CERTIFICATE OF CORRECTION

PATENT NO. : 7,732,507 B2
APPLICATION NO. : 10/540176
DATED : June 8, 2010
INVENTOR(S) : Aref Jallouli et al.

Page 1 of 1

It is certified that error appears in the above-identified patent and that said Letters Patent is hereby corrected as shown below:

In claim 13, column 26, lines 16-28, delete chemical drawings and insert

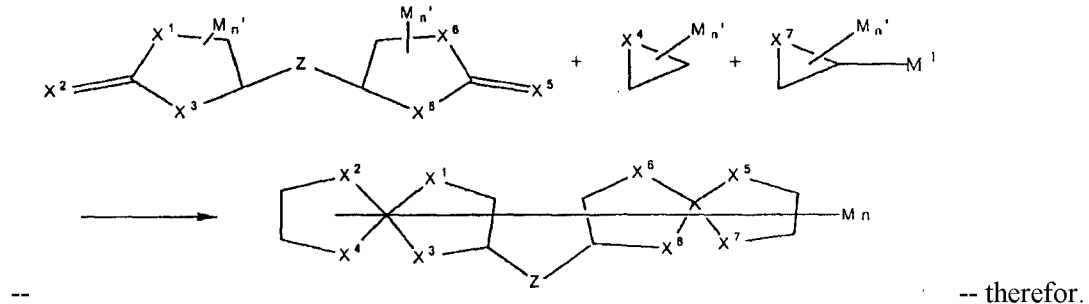

-- therefor.

Signed and Sealed this

Twenty-fourth Day of August, 2010

David J. Kappos
*Director of the United States Patent and Trademark Office*